US009707291B2

(12) United States Patent
Cheminay et al.

(10) Patent No.: US 9,707,291 B2
(45) Date of Patent: Jul. 18, 2017

(54) SINGLE HIGH DOSE OF MVA INDUCES A PROTECTIVE IMMUNE RESPONSE IN NEONATES AND INFANTS

(71) Applicant: Bavarian Nordic A/S, Kvistgaard (DK)

(72) Inventors: Cédric Cheminay, Munich (DE); Ariane Volkmann, Andechs (DE); Paul Chaplin, Gafelfing (DE); Mark Suter, Lucerne (CH)

(73) Assignee: BAVARIAN NORDIC A/S, Kvistgaard (DK)

( * ) Notice: Subject to any disclaimer, the term of this patent is extended or adjusted under 35 U.S.C. 154(b) by 0 days.

(21) Appl. No.: 14/776,881

(22) PCT Filed: Mar. 14, 2014

(86) PCT No.: PCT/EP2014/000693
§ 371 (c)(1),
(2) Date: Sep. 15, 2015

(87) PCT Pub. No.: WO2014/139687
PCT Pub. Date: Sep. 18, 2014

(65) Prior Publication Data
US 2016/0030551 A1 Feb. 4, 2016

Related U.S. Application Data

(60) Provisional application No. 61/788,722, filed on Mar. 15, 2013.

(51) Int. Cl.
| | |
|---|---|
| *A61K 39/285* | (2006.01) |
| *A61K 39/12* | (2006.01) |
| *A61K 39/165* | (2006.01) |
| *A61K 39/00* | (2006.01) |

(52) U.S. Cl.
CPC ........... *A61K 39/285* (2013.01); *A61K 39/12* (2013.01); *A61K 39/165* (2013.01); *A61K 2039/5256* (2013.01); *A61K 2039/545* (2013.01); *A61K 2039/55* (2013.01); *A61K 2039/70* (2013.01); *C12N 2710/24034* (2013.01); *C12N 2710/24043* (2013.01); *C12N 2710/24134* (2013.01); *C12N 2710/24143* (2013.01); *C12N 2760/18434* (2013.01)

(58) Field of Classification Search
CPC .............. A61K 2300/00; A61K 39/12; A61K 2039/53; A61K 2039/545; A61K 2039/5254; A61K 2039/5252; A61K 9/0019; A61K 39/285; A61K 39/275; C12N 7/00; C12N 15/86; C12N 2710/24134; C12N 2710/24121; C12N 2710/24141; C07K 14/005
See application file for complete search history.

(56) References Cited

U.S. PATENT DOCUMENTS

| | | | | |
|---|---|---|---|---|
| 5,211,114 A | * | 5/1993 | Chaplin | E21B 15/003 104/134 |
| 5,471,902 A | * | 12/1995 | Chaplin | G10C 3/10 84/202 |
| 6,761,893 B2 | * | 7/2004 | Chaplin | A61K 39/285 424/199.1 |
| 6,913,752 B2 | * | 7/2005 | Chaplin | A61K 39/285 424/199.1 |
| 7,097,842 B2 | * | 8/2006 | Suter | A61K 39/245 424/199.1 |
| 7,189,536 B2 | * | 3/2007 | Chaplin | A61K 39/285 424/1.11 |
| 7,335,364 B2 | * | 2/2008 | Chaplin | A61K 39/285 424/199.1 |
| 7,384,644 B2 | * | 6/2008 | Chaplin | A61K 39/285 424/184.1 |
| 7,445,924 B2 | * | 11/2008 | Chaplin | A61K 39/285 424/232.1 |
| 7,459,270 B2 | * | 12/2008 | Chaplin | A61K 39/285 424/199.1 |
| 7,501,127 B2 | * | 3/2009 | Howley | C07K 14/005 424/199.1 |
| 7,628,980 B2 | * | 12/2009 | Suter | A61K 39/245 424/199.1 |
| 7,892,533 B2 | * | 2/2011 | Suter | A61K 39/245 424/199.1 |
| 7,897,156 B2 | * | 3/2011 | Ackermann | A61K 39/245 424/232.1 |
| 7,923,017 B2 | * | 4/2011 | Chaplin | A61K 39/285 424/184.1 |

(Continued)

FOREIGN PATENT DOCUMENTS

| | | |
|---|---|---|
| WO | WO03/088994 A2 | 10/2003 |
| WO | WO2009/152969 A1 | 12/2009 |

OTHER PUBLICATIONS

Virapur. TCID50 Assay Protocol. http://www.virapur.com/protocols/TCID50%20Protocol.pdf. Jan. 20, 2011.*
"Immunization Schedules for Infants and Children." CDC. http://www.cdc.gov/vaccines/parents/downloads/parent-ver-sch-0-6yrs-bw.pdf. Updated May 4, 2016.*
Rosario M, Fulkerson J, Soneji S, Parker J, Im EJ, Borthwick N, Bridgeman A, Bourne C, Joseph J, Sadoff JC, Hanke T. Safety and immunogenicity of novel recombinant BCG and modified vaccinia virus Ankara vaccines in neonate rhesus macaques. J Virol. Aug. 2010;84(15):7815-21. doi: 10.1128/JVI.00726-10. Epub May 19, 2010.*

(Continued)

*Primary Examiner* — Rachel B Gill

(57) ABSTRACT

The invention relates to compositions and methods for inducing a protective immune response against a poxvirus in a human neonate or infant of less than 6 months of age. The invention encompasses administering a single high dose of an MVA to a human neonate or infant of less than 6 months of age, wherein the administration induces protective T- and B-cell responses against a poxvirus in the human neonate or infant.

22 Claims, 9 Drawing Sheets

(56) References Cited

U.S. PATENT DOCUMENTS

| | | | | |
|---|---|---|---|---|
| 7,939,086 B2* | 5/2011 | Chaplin | ............... | A61K 39/285 424/184.1 |
| 7,964,395 B2* | 6/2011 | Chaplin | ............... | A61K 39/285 424/184.1 |
| 7,964,396 B2* | 6/2011 | Chaplin | ............... | A61K 39/285 424/184.1 |
| 7,964,398 B2* | 6/2011 | Chaplin | ............... | A61K 39/285 424/184.1 |
| 8,021,669 B2* | 9/2011 | Howley | ............... | C07K 14/005 424/199.1 |
| 8,029,800 B2* | 10/2011 | Howley | ............... | C07K 14/005 424/199.1 |
| 8,163,293 B2* | 4/2012 | Chaplin | ............... | A61K 39/245 424/199.1 |
| 8,197,822 B2* | 6/2012 | Howley | ............... | C07K 14/005 424/199.1 |
| 8,198,088 B2* | 6/2012 | Howley | ............... | C07K 14/005 424/199.1 |
| 8,236,560 B2* | 8/2012 | Chaplin | ............... | A61K 39/285 424/184.1 |
| 8,268,325 B2* | 9/2012 | Chaplin | ............... | A61K 39/285 424/199.1 |
| 8,268,329 B2* | 9/2012 | Chaplin | ............... | A61K 39/285 424/199.1 |
| 8,309,098 B2* | 11/2012 | Howley | ............... | C07K 14/005 424/199.1 |
| 8,323,661 B2* | 12/2012 | Howley | ............... | C07K 14/005 424/199.1 |
| 8,372,622 B2* | 2/2013 | Suter | ............... | A61K 39/245 424/199.1 |
| 8,470,598 B2* | 6/2013 | Chaplin | ............... | A61K 39/285 424/184.1 |
| 8,808,709 B2* | 8/2014 | Chaplin | ............... | A61K 39/285 424/232.1 |
| 9,265,823 B2* | 2/2016 | Chaplin | ............... | A61K 39/285 |
| 2003/0202988 A1* | 10/2003 | Chaplin | ............... | A61K 39/285 424/232.1 |
| 2003/0206926 A1* | 11/2003 | Chaplin | ............... | A61K 39/285 424/232.1 |
| 2003/0215466 A1* | 11/2003 | Chaplin | ............... | A61K 39/285 424/232.1 |
| 2003/0224018 A1* | 12/2003 | Ackermann | ............... | A61K 39/245 424/229.1 |
| 2005/0214323 A1* | 9/2005 | Chaplin | ............... | A61K 39/285 424/232.1 |
| 2005/0260156 A1* | 11/2005 | Suter | ............... | A61K 39/245 424/85.7 |
| 2005/0271688 A1* | 12/2005 | Chaplin | ............... | A61K 39/285 424/232.1 |
| 2006/0127984 A1* | 6/2006 | Ackermann | ............... | A61K 39/245 435/69.1 |
| 2006/0188961 A1* | 8/2006 | Howley | ............... | C07K 14/005 435/69.1 |
| 2006/0280758 A1* | 12/2006 | Chaplin | ............... | A61K 39/285 424/232.1 |
| 2008/0089907 A1* | 4/2008 | Chaplin | ............... | A61K 39/285 424/199.1 |
| 2008/0317778 A1* | 12/2008 | Chaplin | ............... | A61K 39/285 424/205.1 |
| 2009/0017536 A1* | 1/2009 | Chaplin | ............... | A61K 39/285 435/349 |
| 2009/0104224 A1* | 4/2009 | Ackermann | ............... | A61K 39/245 424/199.1 |
| 2009/0169579 A1* | 7/2009 | Chaplin | ............... | A61K 39/285 424/199.1 |
| 2010/0011451 A1* | 1/2010 | Chaplin | ............... | C12Q 1/701 800/3 |
| 2010/0048683 A1* | 2/2010 | Suter | ............... | A61K 39/245 514/44 R |
| 2010/0119545 A1* | 5/2010 | Chaplin | ............... | A61K 39/285 424/199.1 |
| 2010/0183663 A1* | 7/2010 | Howley | ............... | C07K 14/005 424/199.1 |
| 2010/0196992 A1* | 8/2010 | Howley | ............... | C07K 14/005 435/235.1 |
| 2010/0279386 A1* | 11/2010 | Chaplin | ............... | A61K 39/285 435/239 |
| 2011/0052627 A1* | 3/2011 | Chaplin | ............... | A61K 39/165 424/199.1 |
| 2011/0135683 A1* | 6/2011 | Chaplin | ............... | A61K 39/245 424/199.1 |
| 2011/0142877 A1* | 6/2011 | Chaplin | ............... | A61K 39/285 424/199.1 |
| 2011/0159032 A1* | 6/2011 | Suter | ............... | A61K 39/245 424/199.1 |
| 2011/0172407 A1* | 7/2011 | Chaplin | ............... | C12Q 1/701 536/24.33 |
| 2011/0182932 A1* | 7/2011 | Chaplin | ............... | A61K 39/285 424/199.1 |
| 2011/0182933 A1* | 7/2011 | Chaplin | ............... | A61K 39/285 424/199.1 |
| 2011/0217757 A1* | 9/2011 | Chaplin | ............... | A61K 39/285 435/239 |
| 2011/0306093 A1* | 12/2011 | Howley | ............... | C07K 14/005 435/69.3 |
| 2012/0009214 A1* | 1/2012 | Howley | ............... | C07K 14/005 424/199.1 |
| 2012/0014922 A1* | 1/2012 | Howley | ............... | C07K 14/005 424/93.2 |
| 2012/0015423 A1* | 1/2012 | Howley | ............... | C07K 14/005 435/235.1 |
| 2012/0107359 A1* | 5/2012 | Chaplin | ............... | A61K 39/285 424/232.1 |
| 2012/0135032 A1* | 5/2012 | Chaplin | ............... | A61K 39/21 424/199.1 |
| 2012/0183574 A1* | 7/2012 | Chaplin | ............... | A61K 39/245 424/199.1 |
| 2012/0276613 A1* | 11/2012 | Chaplin | ............... | A61K 39/285 435/235.1 |
| 2012/0328650 A1* | 12/2012 | Chaplin | ............... | A61K 39/285 424/199.1 |
| 2014/0322265 A1* | 10/2014 | Chaplin | ............... | A61K 39/07 424/199.1 |
| 2014/0341946 A1* | 11/2014 | Chaplin | ............... | A61K 39/285 424/199.1 |
| 2015/0174238 A1* | 6/2015 | Steigerwald | ............... | C12N 15/86 424/232.1 |
| 2015/0209421 A1* | 7/2015 | Cheminay | ............... | A61K 39/155 424/186.1 |
| 2016/0030551 A1* | 2/2016 | Cheminay | ............... | A61K 39/12 424/199.1 |

OTHER PUBLICATIONS

Hatherill et al., Safety and Immunogenicity of MVA85A Prime and Bacille Calmette-Guerin Boost Vaccination (MVA(TB)029), Clinical Trials.gov. Jan. 2013.

Walsh et al., Safety and Immunogenicity of Modified Vaccinia Ankara in Hematopoietic Stem Cell Transplant Recipients: A Randomized, Controlled Trial, Journal of Infectious Diseases, 207: 1888-97. Mar. 12, 2013.

Zhu et al., Evaluation of Recombinant Vaccinia Virus-Measles Vaccines in Infant Rhesus Macaques with Preexisting Measles Antibody, Virology 276: 202-213 (2000).

Van Rompay et al. Immunization of Newborn Rhesus Macaques with Simian Immunodeficiency Virus (SIV) Vaccines prolongs Survival after Oral Challenge with Virulent SIVmac251, Journal of Virology, 77: 179-190.

Scriba et al., Dose-Finding Study of the Novel Tuberculosis Vaccine, MVA85A, in Healthy BCG-Vaccinated Infants, Journal of Infectious Diseases, 203: 1832-43 (2011).

Marthas et al., Partial efficacy of a VSV-SIV/MVA-SIV vaccine regimen against oral SIV challenge in infant macaques, Vaccine, 29: 3124-3137 (2011).

(56) References Cited

OTHER PUBLICATIONS

International Search Report and Written Opinion of the International Search Authority for PCT/EP2014/000693, dated Jun. 24, 2014.

* cited by examiner

SINGLE HIGH DOSE OF MVA INDUCES A PROTECTIVE IMMUNE RESPONSE IN NEONATES AND INFANTS

This application is a National Phase application under 35 U.S.C. §371 of International Application No. PCT/EP2014/000693, filed Mar. 14, 2014, and claims the benefit under 35 U.S.C. §119(e) of U.S. Provisional Patent Application 61/788,722 filed Mar. 15, 2013, the disclosures of which are incorporated by reference herein in their entirety.

The present invention relates to a method for inducing a protective immune response against a poxvirus in a human neonate or infant of less than 6 months of age comprising administering a dose of at least $10^8$ TCID$_{50}$ of an MVA to a human neonate.

BACKGROUND OF THE INVENTION

There are only three vaccines that are licensed globally for immunization at birth: Bacille Calmette-Guérin (BCG) to prevent tuberculosis, oral Polio vaccine (OPV), and hepatitis B vaccine (HBV). Sanchez-Schmitz et al., *Sci. Transl. Med.* 3, 90ps27 (2011). BCG is a single-dose vaccine of freeze-dried, live *Mycobacterium bovis*. Id. OPV is a single-dose vaccine of a live-attenuated poliovirus. Id. HBV vaccine is a recombinant hepatitis B surface antigen expressed in yeast that is administered with Alum in three-doses, starting at birth. Id. Thus, two of these are live, replicating vaccines, and the other is a recombinant protein given in three doses.

The immaturity of the immune system in newborns has been a major bottleneck to develop safe and effective vaccines at this age. Under the current vaccination schedule for infants, only the Hepatitis B vaccine is recommended at birth, while others are given later during infancy (first 12 months, e.g. rotavirus, inactivated poliovirus vaccine), or are only recommended at 12 months or older (e.g. measles/mumps/rubella vaccine), although in all cases multiple vaccinations are required during infancy/childhood to induce high levels of protection. Sanchez-Schmitz et al., *Sci.*, there is a time span of six to nine months after birth with increased susceptibility to diseases that could be prevented by vaccines. Id. Smallpox, AIDS, malaria, tuberculosis, and other diseases occur in young children with a rapid and often severe disease progression. Even for childhood diseases such as RSV or measles, vaccines do not exist or cannot be administered before 9 months of age. Consequently, vaccination of neonates (within first 4 weeks) and/or a reduced or more effective schedule in infants would be a major advance in reducing mortality and morbidity associated with infectious diseases.

It is generally accepted that newborns mount mainly $T_H2$ biased T-cell responses and produce no or only low levels of antibodies with limited affinity. In addition, these responses are of shorter duration than in adults. Adkins et al., *Nat. Rev. Immunol.* 4, 553-564 (2004); Marshall-Clarke et al., *Immunol. Today* 21, 35-41 (2000); Siegrist, C. A., *Vaccine* 19, 3331-3346 (2001).

However, under certain circumstances, such as activation of pattern recognition receptors or during certain viral infections, newborn mice can mount protective T-cell responses over time, indicating the potential for neonatal immunization. Forsthuber et al., *Science* 271, 1728-1730 (1996); Sarzotti et al., *Science* 271, 1726-1728 (1996).

Parallel to the development of adjuvants improving existing vaccines (Gracia et al., *Vaccine* 29, 1595-1604 (2011); Kamath et al., *PLoS. One.* 3, e3683 (2008)), new antigen delivery systems like DNA vaccines (Hassett et al., *J. Virol.* 74, 2620-2627 (2000); Rigato et al., *Virology* 406, 37-47 (2010)) and the three attenuated replicating bacterial strains *Salmonella enteric* (Ramirez et al., *Vaccine* 28, 6065-6075 (2010)), *Listeria monocytogenes* (Kollmann et al., *J. Immunol.* 178, 3695-3701 (2007)), and BCG (Nascimento et al., *Microbes. Infect.* 10, 198-202 (2008); Ranganathan et al., *Vaccine* 28, 152-161 (2009)) were shown to induce efficient immune responses when administered in one week old mice or even at birth. However, only live attenuated replicating vaccines induced protection against lethal infections, and were generally effective only after several immunizations and thus at a stage with a progressed immunological maturity. Hence, replicative vaccines require substantial time to induce successful protection, and the risk of uncontrolled disseminated infections of live attenuated replicating vaccines still represent major limitations (Galen et al., *Immunol. Cell Biol.* 87, 400-412 (2009); Johnson et al., *Microbiol. Immunol.* 55, 304-317 (2011); Li et al., *Zhonghua Er. Ke. Za Zhi.* 48, 65-68 (2010); Liu et al., *Immunol. Rev.* 239, 62-84 (2011)).

Modified Vaccinia virus Ankara (MVA) has been administered to over 100,000 individuals during the smallpox eradication campaign without any complications. However, MVA still represents a complex mixture of viruses with different levels of attenuation and immunogenicity. Suter et al., *Vaccine* 27, 7442-7450 (2009). The plaque-purified MVA developed by Bavarian Nordic (MVA-BN) completely fails to replicate in mammals including humans and is safe even in immune-compromised hosts. Id. Besides its excellent safety profile, MVA is highly immunogenic in humans (Vollmar et al., *Vaccine* 24, 2065-2070 (2006)) and its efficacy has been proven in several smallpox animal models such as Ectromelia virus (ECTV), rabbitpox or monkeypox (Garza et al., *Vaccine* 27, 5496-5504 (2009); Samuelsson et al., *J. Clin. Invest* 118, 1776-1784 (2008); Stittelaar at al., *J. Virol.* 79, 7845-7851 (2005)). Another major advantage of MVA is its capacity to support the genetic insertion of several antigens (Timm et al., *Vaccine* 24, 4618-4621 (2006)) that could concomitantly induce protection against other infectious diseases or cancer ((Harrer et al. *Antivir. Ther.* 10, 285-300 (2005); Mandl et al., *Cancer Immunol. Immunother.* (2011); Meyer et al., *Cancer Immunol. Immunother.* 54, 453-467 (2005)).

ECTV (the causative agent of mousepox) in mice is a good model system for human poxvirus infection. Esteban et al., Journal of General Virology (2005), 86, 2645-2659. The course of disease is very similar for mousepox and smallpox, including the entry route, the high infectivity at low doses, the development of viremia, the restricted host range, and the delayed but fatal outcome. Therefore, mousepox can be regarded as a valuable small animal model for human smallpox and, in general, as a model for acute, fatal viral diseases. Lauterbach et al., PLoS ONE, Volume 5(3): e9659 (2010).

The pathogenesis of ECTV infection in mice, with localized replication and systemic spread, is similar to the pathogenesis of Variola virus in humans. Chapman et al., Vet Pathol 2010 47: 852 (2010). A comparison of short-term and postexposure protection in mice infected with VACV-WR and ECTV suggested that ECTV infection more closely resembles human smallpox. Paran et al., The Journal of Infectious Diseases; 199:39-48 (2009).

The vaccination of mice with MVA at birth is safe and induces an increase of FLT3 ligand, leading to an accelerated development of plasmacytoid dendritic cells (pDC) and activation of conventional (c) DC resulting in improved resistance against heterologous viral infection. (Franchini at al., *J. Immunol.* 172, 6304-6312 (2004), Vollstedt et al., Eur J Immunol. 34: 1849-1860 (2004) Vollstedt et al., Eur J Immunol. 36: 1231-1240 (2006). Vaccination of one or two-day old mice with $2.5 \times 10^7$ TCID$_{50}$ of MVA protected most mice against challenge with a lethal dose of herpes simplex virus 1 (HSV-1) at 7-8 days after vaccination and protected most mice against challenge with a lethal dose of vaccinia Western Reserve (VV-WR) at 4 weeks after immunization, when the mice were considered adults. WO 03/088994A2. To determine the virus dose needed for maximal induction of CD11c+ cells, graded doses of MVA were tested. Maximal numbers of CD11c+ cells were detected after treatment with $2.5 \times 10^6$ TCID$_{50}$ of virus; whereas, doses below and above this were less effective. Id. Thus, $2.5 \times 10^6$ TCID$_{50}$ was considered to be the optimal dose of MVA for the vaccination of neonates.

Consequently, a need in the art exists for compositions and methods for vaccination of neonates to achieve strong T-cell and antibody responses and protection against pathogens. The invention fulfills this need.

SUMMARY OF THE INVENTION

The invention encompasses compositions and methods for inducing a protective immune response against a poxvirus in a human neonate or infant of less than 6 months of age. In one embodiment, the invention encompasses administering a dose of at least $10^8$ TCID$_{50}$ of an MVA to a human neonate or infant of less than 6 months of age, wherein the administration induces protective T- and B-cell responses against a poxvirus in the human neonate prior to 6 months of age, preferably within 2 weeks of the administration. Most preferably, the immune response is induced in the absence of a second administration of the MVA.

In various embodiments, the administration is administered to a human neonate or infant of less than 2 months of age or within 72 hours after birth.

Preferably, the administration induces protective T- and B-cell responses against a poxvirus. Most preferably, the administration induces protective T- and B-cell responses against smallpox.

In some embodiments, the invention encompasses administering one or more boosting administrations of the MVA.

In some embodiments, the MVA is a recombinant MVA. In some embodiments, the administration induces T- and B-cell responses against a heterologous antigen encoded by the recombinant MVA.

DETAILED DESCRIPTION OF THE INVENTION

Figure 1:
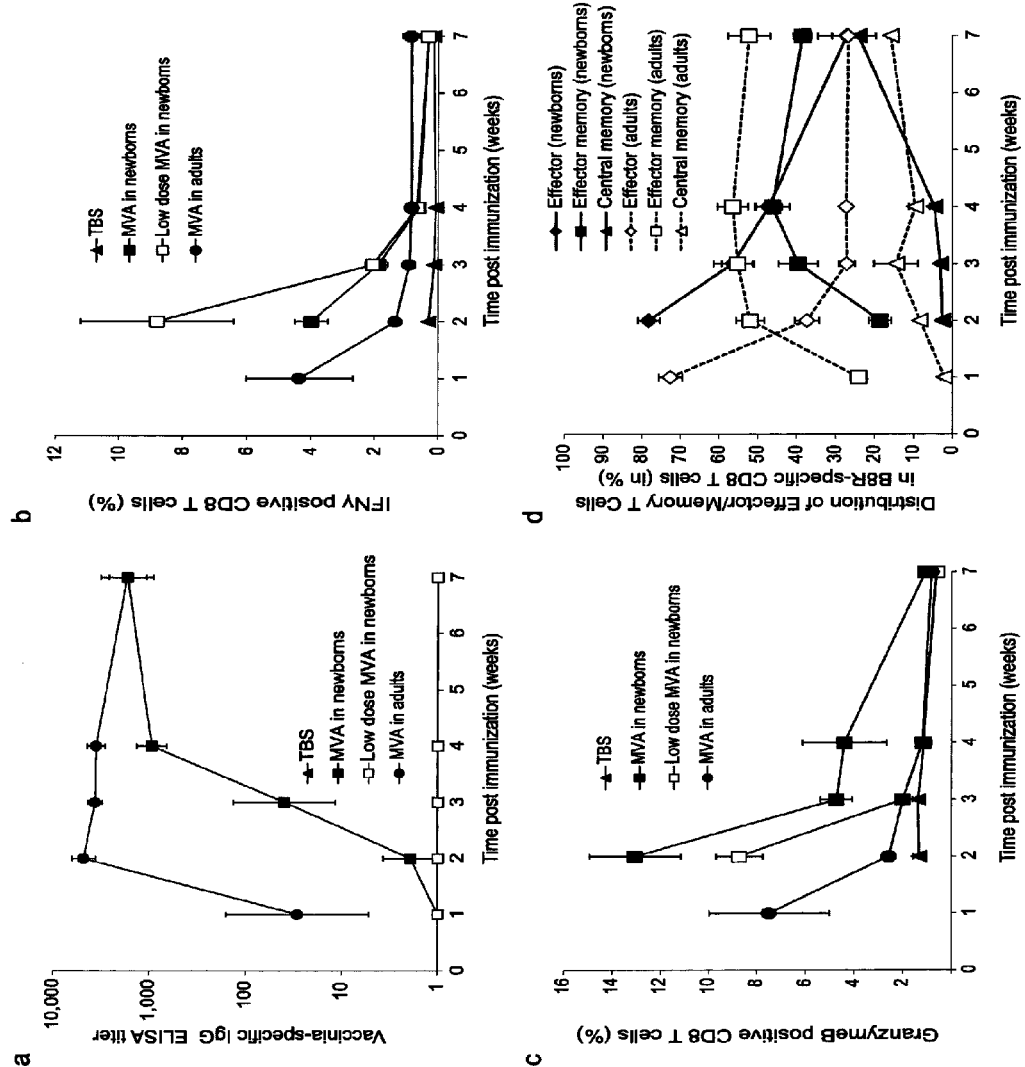
FIGS. 1*a-d* show a comparison of the vaccinia-specific immune responses in newborn versus adult mice after a single MVA-BN vaccination. Newborn or adult C57BL/6 mice were immunized with a high dose ($1 \times 10^8$ TCID$_{50}$) or a low dose ($2 \times 10^6$ TCID$_{50}$) of MVA. Animals were bled and sacrificed 1, 2, 3, 4 or 7 weeks post-immunization. (a) Vaccinia-specific IgG in serum was measured by ELISA. Geometric mean titers+/−standard error of the mean (GMT+/−SEM) are shown. (b) Percentage of B8R-specific IFNγ-secreting CD8+ T-cells in spleen was determined by flow cytometry. Mean percentages+/−standard error of the mean (SEM) are shown. (c) Percentage of granzyme B-expressing CD8+ T-cells in spleen was determined by flow cytometry. Mean percentages+/−standard error of the mean (SEM) are shown. (d) Distribution (in %) of effector (CD44$^{high}$CD62L$^-$CD127$^-$), effector memory (CD44$^{high}$CD62L$^-$CD127$^+$) and central memory (CD44$^{high}$CD62L$^+$CD127$^+$) cells within the B8R-specific CD8+ T-cell population isolated from spleen was measured by flow cytometry. Mean percentages+/−standard error of the mean (SEM) are shown. The distribution was identical in newborn mice immunized with the two different doses of MVA-BN, only the $1 \times 10^8$ TCID$_{50}$ dose is shown. Analysis in one week old mice was not possible due to insufficient numbers of CD8+ T-cells in the spleen.

The threat of a potential bioterrorism attack or emergence of zoonotic poxviruses in the human population has prompted several efforts to develop a safer third generation smallpox vaccine suitable for at-risk populations contraindicated for ACAM2000™, the smallpox vaccine currently licensed in the USA. However, at-risk populations include not only immuno-compromised individuals such as HIV patients or individuals suffering from skin disorders like atopic dermatitis, but also children less than one year old due to the immaturity of their immune system. MVA-BN with its excellent safety profile as a replication-deficient live virus has previously been shown to enhance broad-spectrum resistance to viral infections in the first week of life in mice. Franchini, *J. Immunol.* 172, 6304-6312 (2004).

Naïve neonates are considered difficult if not impossible to protect against fatal infections shortly after birth. However, by increasing the vaccination dose to a dose of $1\times10^8$ $TCID_{50}$ of Modified Vaccinia Ankara (MVA), it was demonstrated that a single immunization of mice at birth induced fully functional T- and B-cell responses that rapidly conferred full protection against a lethal orthopoxvirus challenge. Surprisingly, protection is induced within 2 weeks and is mainly T-cell-dependent. Furthermore, persisting immunological T-cell memory and neutralizing antibodies were obtained with this single vaccination. Thus, MVA administered as early as at birth induces immediate and long-term protection against fatal diseases and appears attractive as a platform for early childhood vaccines.

A single vaccination of mice with MVA at birth not only induces innate, but also adaptive immune responses including effector and long term memory T-cells as well as neutralizing antibody responses. Importantly, within two weeks after vaccination the adaptive immune response fully protects mice against a lethal intranasal challenge with ECTV.

Here, it is demonstrated that an important role for T-cells exists in newborn mice. When immunized with a low dose of $2\times10^6$ $TCID_{50}$ of MVA, a strong cytotoxic T-cell response was induced, which led to partial protection from ECTV challenge in the absence of detectable antibody responses. Complete protection was only achieved after vaccination with a high dose of $1\times10^8$ $TCID_{50}$ of MVA, a dose that also induces B-cell responses. This was confirmed in T11μMT transgenic mice, in which partial protection showed that B-cells are also required in order to achieve complete protection after a single vaccination with MVA at birth.

The invention encompasses compositions and methods for inducing a protective immune response against a poxvirus in a human neonate or infant. In one embodiment, the invention encompasses administering a dose of at least $10^8$ $TCID_{50}$ of an MVA to a human neonate or infant. The MVA can be administered to a human neonate or infant prior to the full maturation of the immune system.

The invention further encompasses MVA for use in inducing a protective immune response against a poxvirus in a human neonate or infant.

The invention also encompasses MVAs for use in vaccinating a human neonate or infant. The invention also encompasses the use of MVAs as vaccines for treating a human neonate or infant and the use of MVAs in the preparation of vaccines or medicaments for treating or vaccinating a human neonate or infant.

Human Neonates and Infants

Within the context of this invention, the term "human neonate" refers to a newborn human less than 1 month of age and the term "human infant" refers to a human between birth and 1 year of age. Preferably, the human neonate is less than 4 weeks of age, less than 3 weeks of age, less than 2 weeks of age, or less than 1 week of age. More preferably, the human neonate is less than 6, 5, 4, 3, 2, or 1 days of age.

In one embodiment, a dose of MVA is administered to a human neonate. In various embodiments, a dose of MVA is administered to a human neonate of less than 4 weeks of age, less than 3 weeks of age, less than 2 weeks of age, or less than 1 week of age. In various embodiments, a dose of MVA is administered to a human neonate of less than 6, 5, 4, 3, 2, or 1 days of age. In preferred embodiments, a dose of MVA is administered to a human neonate within 3, 2, or 1 days of birth.

In one embodiment, a dose of MVA is administered to a human infant of less than 6, 5, 4, 3, 2, or 1 months of age. In various embodiments, a dose of MVA is administered to a human infant of less than 8 weeks of age, less than 7 weeks of age, less than 6 weeks of age, or less than 5 weeks of age. In preferred embodiments, a dose of MVA is administered to a human infant of less than 2 months of age.

Modified Vaccinia Ankara (MVA) Viruses

The invention encompasses any and all MVA viruses. Preferred MVA viruses include MVA variant strains such as MVA-BN (deposited at the European Collection of Animal Cell Cultures, Vaccine Research and Production Laboratory, Public Health Laboratory Service, Centre for Applied Microbiology and Research, Porton Down, Salisbury, Wiltshire SP4 0JG, United Kingdom (ECACC) on Aug. 30, 2000, under Accession No. V00083008), MVA-575 (deposited at ECACC on Dec. 7, 2000, under Accession No. V00120707), and MVA-572 (deposited at ECACC on Jan. 27, 1994 under Accession No. V94012707). Derivatives of the deposited strain are also preferred.

Preferably, the MVA has the capability of reproductive replication in vitro in chicken embryo fibroblasts (CEF) or other avian cell lines or in vivo in embryonated eggs, but no capability of reproductive replication in human cells in which MVA 575 or MVA 572 can reproductively replicate. Most preferably, the MVA has no capability of reproductive replication in the human keratinocyte cell line HaCaT, the human embryo kidney cell line 293 (also referred to as HEK293), the human bone osteosarcoma cell line 143B, and the human cervix adenocarcinoma cell line HeLa.

In preferred embodiments, the Modified vaccinia virus Ankara (MVA) virus is characterized by having the capability of reproductive replication in vitro in chicken embryo fibroblasts (CEF) and by being more attenuated than MVA-575 in the human keratinocyte cell line HaCaT, in the human bone osteosarcoma cell line 143B, and in the human cervix adenocarcinoma cell line HeLa. Preferably, the MVA virus is capable of an amplification ratio of greater than 500 in CEF cells. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

Recombinant MVAs

The invention encompasses recombinant MVA viruses generated with any and all MVA viruses. In one embodiment, the recombinant MVA virus is a recombinant MVA-BN virus. The recombinant MVA virus comprises at least one heterologous nucleic acid sequence. In the context of this invention, the term "heterologous" nucleic acid sequence refers to a nucleic acid sequence that is not naturally found in the MVA.

Preferably, the heterologous nucleic acid sequence is a sequence coding for at least one antigen, antigenic epitope, and/or a therapeutic compound. The antigenic epitopes and/or the antigens can be antigenic epitopes and/or antigens of an infectious agent. The infectious agents can be viruses, fungi, pathogenic unicellular eukaryotic or prokaryotic organisms, and parasitic organisms. In some embodiments, the infectious agent is a virus selected from any of the following: Rotavirus, Rubella virus, Poliovirus, Influenza virus, Flavivirus (particularly Dengue virus and Yellow Fever virus), Paramyxovirus (particularly measles virus, mumps virus, and respiratory syncytial virus (RSV)), Hepatitis virus (particularly Hepatitis A, B, and C viruses), Human immunodeficiency virus (particularly HIV-1), Filovirus (particularly Ebola virus and Marburg virus) or from other viruses causing hemorrhagic fever. In some embodiments, the infectious agent is a bacterium selected from any of the following: *Bacillus anthracis*, meningococcus, pneumococcus, *Haemophilus influenza, Corynebacterium diphtheriae, Clostridium tetani, Burkholderia, Francisella tularensis, Coxiella burnetii*, or *Bordetella pertussis*.

Any antigen, including those that induce a T-cell response, can be expressed by the recombinant MVA of the invention. Viral, bacterial, fungal, and cancer antigens are preferred. Preferred antigens are antigens of any of the viruses or bacteria described above. HIV-1 antigens, Dengue virus antigens, anthrax antigens, measles virus antigens, influenza virus antigens, picornavirus antigens, coronavirus antigens and respiratory syncytial virus antigens are particularly preferred antigens. Preferably, the antigen is a foreign antigen or neoantigen. Within the context of this invention, the term "neoantigen" refers to an antigen not naturally expressed by the poxviral vector.

In some embodiments, the administration induces T- and/or B-cell responses against a heterologous antigen encoded by the recombinant MVA. The T-cell response can be an effector and/or long term memory T-cell response. The B-cell response can be a neutralizing antibody response.

Administration

The invention encompasses administration of a dose of an MVA to a human neonate or infant via any route. Preferred routes of administration include subcutaneous (s.c.), intradermal (i.d.), intramuscular (i.m.), in bone marrow (i.bm.) or intravenous (i.v.) injection, oral administration and mucosal administration, especially intranasal administration, or inhalation. The quantity to be administered (dosage) depends on the subject to be treated, considering among other things the condition of the patient, the state of the individual's immune system, the route of administration and the size of the host.

The invention further encompasses MVAs for use as a pharmaceutical composition or vaccine for vaccinating a human neonate or infant, the use of MVAs as pharmaceutical compositions or vaccines for treating a human neonate or infant, and the use of MVAs in the preparation of pharmaceutical compositions or vaccines or medicaments for treating or vaccinating a human neonate or infant.

The pharmaceutical composition, vaccine or medicament can generally include one or more auxiliary substances, such as pharmaceutically acceptable and/or approved carriers, additives, antibiotics, preservatives, adjuvants, diluents and/or stabilizers. Such auxiliary substances can be water, saline, glycerol, ethanol, oil, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

For the preparation of pharmaceutical compositions or vaccines or medicaments, the MVA according to the invention can be converted into a physiologically acceptable form. This can be done based on experience in the preparation of poxvirus vaccines used for vaccination against smallpox (as described by Stickl et al. 1974). The purified virus can be stored at −20° C., or −80° C., frozen in a liquid. Preferably, the virus has a titer of $5 \times 10^8$ TCID50/ml, and can be formulated in a buffered solution, for example, in 10 mM Tris, 140 mM NaCl, at pH 7.4.

The virus formulation can contain additional additives such as mannitol, dextran, sugar, glycine, lactose or polyvinylpyrrolidone or other auxiliary substances, such as antioxidants or inert gas, stabilizers or recombinant proteins (e.g., human serum albumin, or HSA) suitable for in vivo administration.

Alternatively, the vaccine can be produced by stepwise freeze-drying of the virus in a formulation. For example, $10^8$ particles of the virus can be lyophilized in 100 µl to 1 ml of phosphate-buffered saline (PBS) in the presence of 2% peptone and 1% HSA in an ampoule, preferably a glass ampoule. The glass ampoule is then sealed and can be stored between 4° C. and room temperature for several months. However, as long as no need exists the ampoule is stored preferably at temperatures below −20° C.

For vaccination or therapy, the virus can administered either systemically or locally, i.e., parenterally, subcutaneously, intravenously, intramuscularly, intranasally, or by any other path of administration known to the skilled practitioner.

Dose

The invention encompasses a dose of at least $10^8$ TCID$_{50}$ of an MVA administered to a human neonate or infant. Preferably, the dose is at least $10^8$ TCID$_{50}$, $2 \times 10^8$ TCID$_{50}$, $3 \times 10^8$ TCID$_{50}$, $4 \times 10^8$ TCID$_{50}$, $5 \times 10^8$ TCID$_{50}$, $6 \times 10^8$ TCID$_{50}$, $7 \times 10^8$ TCID$_{50}$, $8 \times 10^8$ TCID$_{50}$, $9 \times 10^8$ TCID$_{50}$, or $10^9$ TCID$_{50}$ of an MVA. A particularly preferred dose is $2 \times 10^8$ TCID$_{50}$, $3 \times 10^8$ TCID$_{50}$, $4 \times 10^8$ TCID$_{50}$, $5 \times 10^8$ TCID$_{50}$, $6 \times 10^8$ TCID$_{50}$, $7 \times 10^8$ TCID$_{50}$, $8 \times 10^8$ TCID$_{50}$, $9 \times 10^8$ TCID$_{50}$, or $10^9$ TCID$_{50}$ of an MVA. Especially preferred is a dose of $10^8$ TCID$_{50}$.

The human neonate or infant can be vaccinated with a single administration of the MVA in the absence of any additional ("boosting") administrations. In other embodiments, one or more boosting administrations are administered. In one embodiment, a second administration is given four weeks to eight weeks after the first vaccination administration. Preferably, the second administration is given at 2, 4, 6, or 8 weeks after the first administration. In other embodiments, a third, fourth, fifth, sixth, seventh, eighth, ninth, tenth, or additional administration is given.

The boosting administration can be administered to increase immune response when the initial response decays or to further increase the initial response. Thus, in some embodiments a boosting administration is provided to augment or reestablish a desired level of immune response.

The time between the first and second administrations and between an administration and a subsequent administration can vary. In one embodiment, the time between administrations is two to six weeks. In various embodiments, the time between administrations is at least 2, 4, 6, 8, 10, 12, 15, 30, or 52 weeks. In various embodiments, the time between administrations is at least 1, 3, 6, 9, 12, 24, 36, or 48 months. In various embodiments, the time between administrations is at least 1, 2, 3, 4, 5, 6, 7, 8, 9, or 10 years.

Protective Immune Response

The invention encompasses the induction of a protective immune response against a poxvirus by administration of a dose of an MVA to a human neonate or infant. Preferably the administration induces protective T- and B-cell responses against the poxvirus in the human neonate or infant prior to 6 months of age. Most preferably, the immune response is induced in the absence of a second administration of the MVA. Within the context of this invention, the phrase "the immune response is induced in the absence of a second administration of the MVA" means that the immune response does not depend on the administration of a second (i.e., boosting) dose of the MVA. The immune response is induced by the first administration. Thus, within the context of this invention, the phrase "the immune response is induced in the absence of a second administration of the MVA" does not mean that a second administration is not administered; it only means that a second administration is not required to induce the protective immune response. In some embodiments, a second or subsequent administration is administered. The second or subsequent administration can increase the level of the immune response and/or the longevity of the immune response.

The protective immune response can protect at least 75%, 80%, 90%, 95%, 96%, 97%, 98%, 99% or 100% of the neonates or infants to which the MVA is administered from death and/or disease symptoms.

Preferably, the protective immune response is against a poxvirus, particularly an orthopoxvirus. In some embodiments, the poxvirus is a vaccinia virus or a variola virus. Most preferably, the protective immune response is against smallpox.

Preferably, the protective immune response is induced in the human neonate or infant prior to 6 months of age. More preferably, the protective immune response is induced in the human neonate or infant prior to 5, 4, 3, 2, or 1 months of age. Most preferably, the protective immune response is induced in the human neonate or infant within 4, 3, or 2 weeks of the administration.

Compositions

The invention encompasses pharmaceutical compositions and vaccines comprising at least $10^8$ $TCID_{50}$ of an MVA for administration to an infant or neonate to induce a protective immune response. Preferably, the composition comprises $10^8$ $TCID_{50}$, $2 \times 10^8$ $TCID_{50}$, $3 \times 10^8$ $TCID_{50}$, $4 \times 10^8$ $TCID_{50}$, $5 \times 10^8$ $TCID_{50}$, $6 \times 10^8$ $TCID_{50}$, $7 \times 10^8$ $TCID_{50}$, $8 \times 10^8$ $TCID_{50}$, $9 \times 10^8$ $TCID_{50}$, or $10^9$ $TCID_{50}$ of an MVA. A particularly preferred dose is $2 \times 10^8$ $TCID_{50}$, $3 \times 10^8$ $TCID_{50}$, $4 \times 10^8$ $TCID_{50}$, $5 \times 10^8$ $TCID_{50}$, $6 \times 10^8$ $TCID_{50}$, $7 \times 10^8$ $TCID_{50}$, $8 \times 10^8$ $TCID_{50}$, $9 \times 10^8$ $TCID_{50}$, or $10^9$ $TCID_{50}$ of an MVA. Especially preferred is a dose of $10^8$ $TCID_{50}$.

EXAMPLES

The following examples will further illustrate the present invention. It will be well understood by a person skilled in the art that the provided examples in no way may be interpreted in a way that limits the applicability of the technology provided by the present invention to this examples.

Example 1: Mice

Time-mated C57BL/6J and BALB/c female mice were obtained from Harlan Winkelmann, whereas B-cell receptor/ T11μMT transgenic, activation-induced cytidine deaminase-deficient (AID-deficient), MHC class I/β2m-deficient, T-cell receptor βδ deficient and FLT3-deficient mice on a C57BL/6 background were obtained from the animal facilities of the University Zurich or Bavarian Nordic-Munich. Litters were of mixed gender. Pups were weaned at 4 weeks of age.

Example 2: Vaccines and Challenge Virus

The MVA used was MVA-BN, developed by Bavarian Nordic and deposited at ECACC under Accession No. V00083008 (see above). The recombinant MVA-measles vaccine MVA-mBN85B encodes 3 measles genes: the Fusion-, Hemagglutinin- and Nucleo-proteins. The gene sequences were derived from RNA of measles strain Khartoum SUD/34.97 (Genotype B3). Both viruses were propagated and titrated on primary chicken embryo fibroblasts that were prepared from 11-day-old embryonated, pathogen-free hen eggs (Charles River, Mass., USA) and cultured in RPMI-1640 medium. ECTV strain Moscow was obtained from the American Type Culture Collection (ATCC) under Accession No. VR-1372, and was propagated and titered on Vero C1008 cells (ECACC Accession No. 85020206), maintained in Dulbecco's Modified Eagle's Medium (DMEM; Invitrogen) supplemented with 10% FCS without antibiotics. All viruses were purified through a sucrose cushion.

Example 3: Immunization and Challenge

Mice were immunized subcutaneously within 6-24 hours after birth with 50 μl of viral suspension. 8-weeks old animals were used for the comparison of newborns to adults (i.e., adults were 8-weeks old). $1 \times 10^8$ $TCID_{50}$ MVA or MVA-mBN85B was applied, except for some animals that received either a lower dose ($2 \times 10^6$ $TCID_{50}$) or $1 \times 10^8$ $TCID_{50}$ of UV-inactivated MVA. Samuelsson et al., *J. Clin. Invest.* 118, 1776-1784 (2008). Control animals were treated with TRIS-buffered saline, pH 7.7. For MVA-mBN85B, mice were immunized twice three weeks apart. For immunogenicity studies, animals were bled and sacrificed at different time points and spleens were processed for flow cytometric analyses.

For ECTV challenge, mice were anaesthetized with ketamine/xylamine and virus was applied intranasally in a volume of 25 μl, except for 2-week old animals, which received virus in a volume of 12.5 μl. For each age group and mice strain, the optimal dose inducing 100% death within 2 weeks and with approximately a viral load of 8 $Log_{10}$ pfu in necropsied lung was determined. For 29-day old mice, the optimal dose was $1\times10^4$ $TCID_{50}$ (4 times the $LD_{50}$ determined for adult C57BL/6J mice; Samuelsson et al., *J. Clin. Invest* 118, 1776-1784 (2008)), except for the FLT3-deficient and TCRβδ-deficient mice. In these highly susceptible mice, $1\times10^3$ $TCID_{50}$ of ECTV was sufficient. For 2-week- and 7 week-old mice, the challenge dose was $1\times10^2$ $TCID_{50}$ and $3\times10^4$ $TCID_{50}$, respectively. After challenge, weight loss sickness and death were monitored daily for 21 days. 5 to 7 pups were included in each group and data are representative of two or three experiments.

Example 4: ECTV Plaque Assay

ECTV plaque assay was used to determine the viral load in necropsied lung. Lungs were homogenized and titered on Vero C1008 cells using four-fold serial dilutions starting at 1:100. After 3 days of incubation and a crystal violet staining (Sigma Aldrich), the titer was calculated from the first dilution step that revealed a mean plaque number ≤150.

Example 5: ELISA

Figure 6:
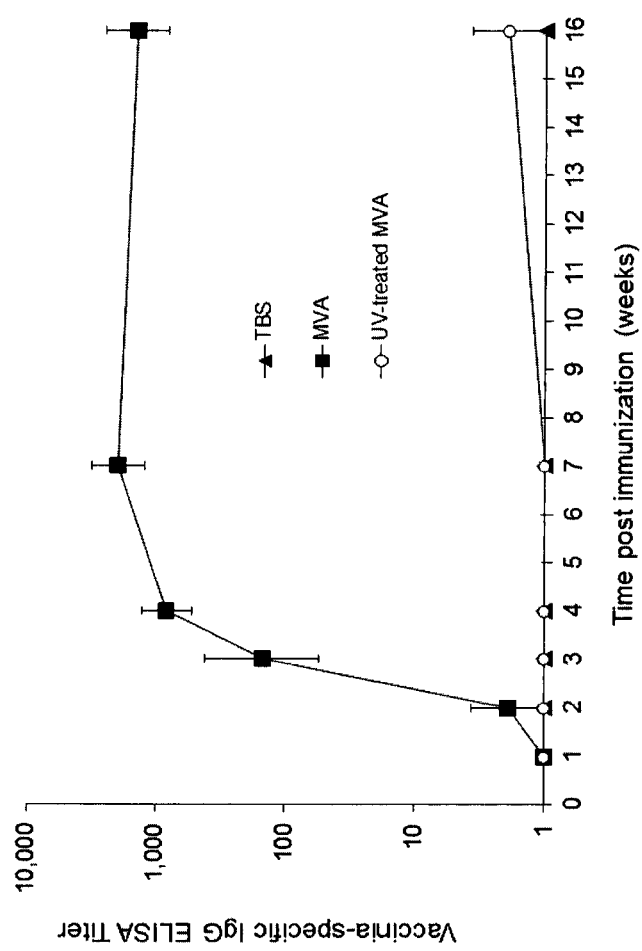
FIG. 6 shows long term vaccinia-specific B-cell responses in newborn mice after a single vaccination with MVA or UV-treated MVA. Newborn C57BL/6 mice were immunized with $1 \times 10^8$ TCID$_{50}$ of MVA or with $1 \times 10^8$ TCID$_{50}$ of UV-treated MVA. Animals were bled and sacrificed 1, 2, 3, 4, 7 or 16 weeks post-immunization. Vaccinia-specific IgG in serum was measured by ELISA. Geometric mean titers+/−standard error of the mean (GMT+/−SEM) are shown.
Figure 7:
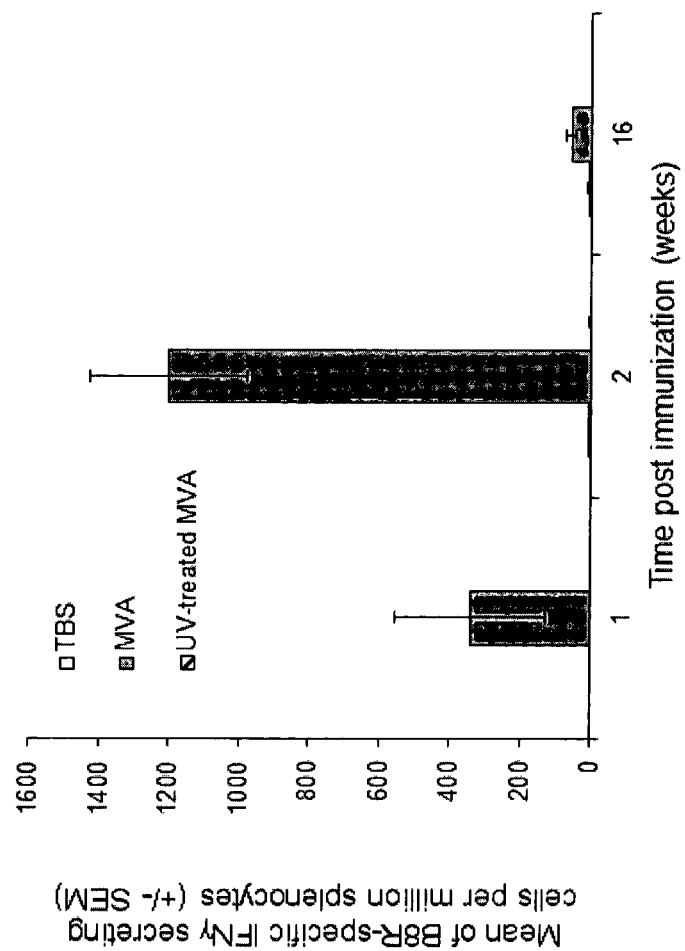
FIG. 7 shows long term vaccinia-specific T-cell responses in newborn mice after a single MVA or UV-treated MVA vaccination. Newborn C57BL/6 mice were immunized with $1 \times 10^8$ TCID$_{50}$ of MVA or with $1 \times 10^8$ TCID$_{50}$ of UV-treated MVA. Animals were sacrificed 1, 2 or 16 weeks post-immunization. Vaccinia-specific T-cells were measured after in vitro stimulation of splenocytes with a B8R-specific peptide and IFNγ-secreting cells were detected by ELISpot. (Mean of stimulation indexes+/−SEM).
Figure 8:
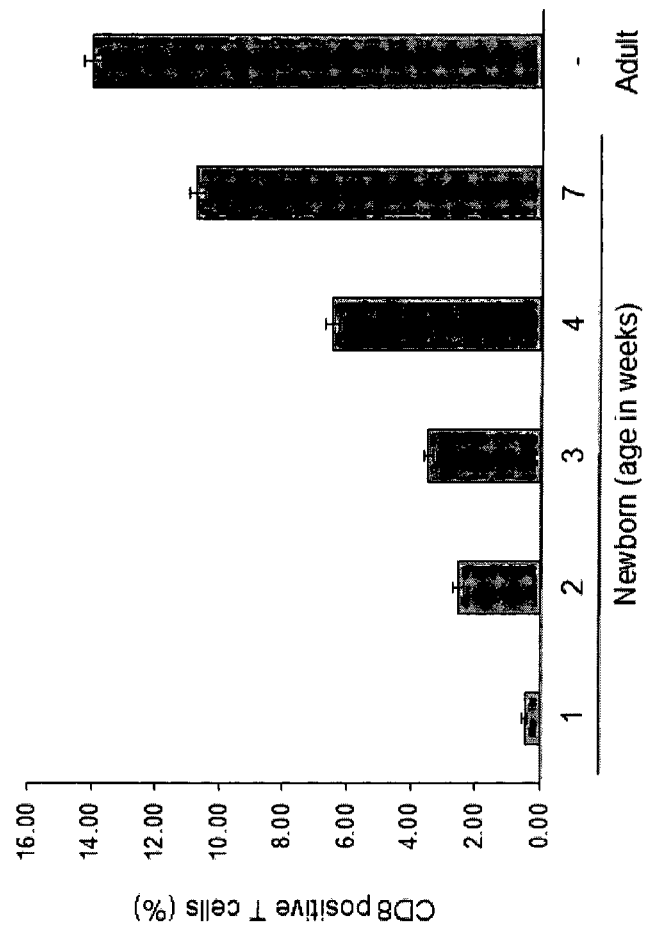
FIG. 8 shows CD8+ T-cell frequency in newborn mice compared to adult mice. For 1-, 2-, 3-, 4- and 7-week old newborn mice, the percentage of CD8+ T-cells in spleen was determined by flow cytometry and compared to adult mice. Mean percentages+/−standard error of the mean (SEM) are shown

Vaccinia-specific serum IgG titers were measured by direct ELISA as described previously. Garza et al., *Vaccine* 27, 5496-5504 (2009). Briefly, 96-well plates were coated overnight with MVA antigen. Test sera were titrated using twofold serial dilutions starting at 1:50. A sheep anti-mouse IgG-HRP (AbD Serotec) was used as detection antibody. The antibody titers were calculated by linear regression and defined as the serum dilution that resulted in an optical density of 0.30 at $OD_{450}$. Measles-specific serum IgG titers were measured with the Enzygnost® ELISA kit (Dade Behring), but using the sheep anti-mouse IgG conjugated to horseradish peroxidase.

Example 6: Plaque Reduction Neutralization Test (PRNT) Assay

Vaccinia-based PRNT assay was performed as described in Garza et al. *Vaccine* 27, 5496-5504 (2009). Briefly, heat-inactivated sera were serially diluted and incubated with vaccinia virus Western Reserve (Advanced Biotechnologies Inc.). After incubation the mixtures were allowed to adsorb on Vero cells for 70 minutes. Then, overlay medium was added and plates were incubated for 24 hours. After staining with Crystal Violet, the neutralizing titer was determined as the serum dilution which was able to neutralize 50% of the mature virus.

Example 7: Flow Cytometry and ELISpot

After erythrolysis, a part of the splenocytes were incubated 5 hours with or without the B8R-peptide (Tscharke et al., *J. Exp. Med.* 201, 95-104 (2005)) (5 μg/ml $B8R_{20-27}$), Coring) in the presence of GolgiPlug™ (BD Biosciences). Cells were then stained with anti-CD8+-eFluor™-450, anti-CD4+-eFluor™-780, anti-CD44-FITC, anti-CD62L-PercP-Cy5.5, anti-CD127-APC, anti-IFNγ-PE-Cy7 (all eBioscience) and anti-Granzyme B-PE (Invitrogen). Intracellular staining was performed after fixation/permeabilization (BD Cytofix/Cytoperm™, BD Biosciences). Flow cytometric analysis was performed using an LSR II (BD Biosciences). Data were analyzed with FlowJo (Tree Star). The rest of the splenocytes were stimulated 20 hours with or without B8R/vaccinia- or N/measles-specific (Halassy et al., *Vaccine* 24, 185-194 (2006); Bergen et al., PLoS one 5(4):e10297, 2010) peptides (5 μg/ml; aa 335-345; N) and IFNγ-secreting cells were detected by ELISpot assay (BD Biosciences). The stimulation index was obtained by subtracting the number of unspecific spots from non-stimulated cells from the number of spots obtained with the specific stimulation.

Example 8: Neutralizing Antibodies as Well as Effector and Long-Term Memory T-Cells are Induced by MVA in Newborn Mice Newborn mice were immunized at birth with a high dose (lx $10^8$ $TCID_{50}$) or low dose ($2×10^8$ $TCID_{50}$) of MVA used previously in newborn mice. Franchini et al., *J. Immunol.* 172, 6304-6312 (2004). Vaccinia-specific IgG antibody responses were determined by enzyme-linked immunosorbent assay (ELISA) performed 1, 2, 3, 4 and 7 weeks post-immunization (FIG. 1*a*). In adult mice, vaccinia-specific antibodies were detectable seven days following a single immunization with $1×10^8$ $TCID_{50}$ of MVA and reached a plateau one week later. Surprisingly, specific IgG responses after a single high dose immunization at birth reached comparable antibody levels, albeit with a delay of 1-2 weeks (FIG. 1*a*). Despite the immaturity of the neonatal immune system, even vaccinia-neutralizing antibodies were induced, although complete sero-conversion was not observed and titers were approximately 10-fold lower than in adult mice (Table 1).

TABLE 1

Vaccinia-specific neutralizing antibody responses

| Age group | Treatment | weeks post immunization | 1 | 2 | 3 | 4 | 7 |
|---|---|---|---|---|---|---|---|
| Newborn | TBS | seroconversion[a] | 0.0 | 0.0 | 0.0 | 0.0 | 0.0 |
| | | Titer[b] | 1.0 | 1.0 | 1.0 | 1.0 | 1.0 |
| | $2 \times 10^6$ $TCID_{50}$ MVA | seroconversion[a] | 0.0 | 0.0 | 0.0 | 0.0 | 0.0 |
| | | Titer[b] | 1.0 | 1.0 | 1.0 | 1.0 | 1.0 |
| | $1 \times 10^8$ $TCID_{50}$ MVA | seroconversion[a] | 0.0 | 16.7 | 33.3 | 66.7 | 66.7 |
| | | Titer[b] | 1.0 | 1.3 | 2.6 | 11.6 | 5.7 |
| Adult | $1 \times 10^8$ $TCID_{50}$ MVA | seroconversion[a] | 33.3 | 100.0 | 66.7 | 100.0 | 00.0 |
| | | Titer[b] | 1.8 | 18.9 | 11.5 | 163.7 | 37.9 |

[a]in percent
[b]geometric mean titer

The B-cell response induced by a single immunization with MVA-BN at birth was still detectable 16 weeks after immunization (FIG. 6) and could be boosted by a second immunization 3 or 4 weeks after birth. As with the B-cell response, a slight delay in the CD8+ T-cell responses induced by immunization with MVA at birth was observed. The vaccinia-specific T-cell response measured by IFNγ intracellular staining 2 weeks post-immunization of newborn mice was similar to the peak response in adult mice observed one week post immunization (FIG. 1*b*). Whereas no antibody response could be detected after vaccination with the low dose of MVA (FIG. 1*a*), the same or even higher levels of T-cell responses were induced by vaccination with the low dose (FIG. 1*b*). The presence of vaccinia-specific T-cells induced by MVA vaccination at birth was confirmed by enzyme-linked immunospot (ELISpot) assay, which detected vaccinia-specific IFN-γ producing cells already one week post immunization (FIG. 7). This early time point is even more remarkable when considering the low number of CD8+ T-cells in the spleen of one week old mice (FIG. 8). T-cell activation was also confirmed by analysis of Granzyme B expression in the CD8+ T-cell population. This effector molecule of cytotoxic T-cells was induced by immunization at birth with both doses of MVA at a similar level of expression as that seen in adults, albeit one week delayed (FIG. 1c). For a more detailed analysis, the vaccinia-specific CD8+ T-cells were subdivided into effector, effector memory and central memory cells based on the differential expression of CD44, CD62L and CD127 as described by Kaech et al., Nat. Immunol. 4, 1191-1198 (2003). As expected, the majority of the vaccinia-specific T-cells were effector cells at the peak of the T-cell response in both newborn and adult mice (FIG. 1d). During the subsequent contraction phase, they acquired similar effector memory or central memory phenotypes in both age groups (FIG. 1d). As for the B-cell response, T-cells specific for MVA were still detectable 16 weeks after neonatal immunization (FIG. 7). No antigen-specific B- and T-cell responses were induced after UV treatment of MVA prior to immunization (FIGS. 6 and 7), revealing the requirement for transcription and protein synthesis of the non-replicating MVA. The lack of antigen-specific B- and T-cell responses after UV treatment was previously shown for Herpes Simplex Virus (Franchini et al. J. Virol. 75, 83-89 (2001)).

Figure 2:
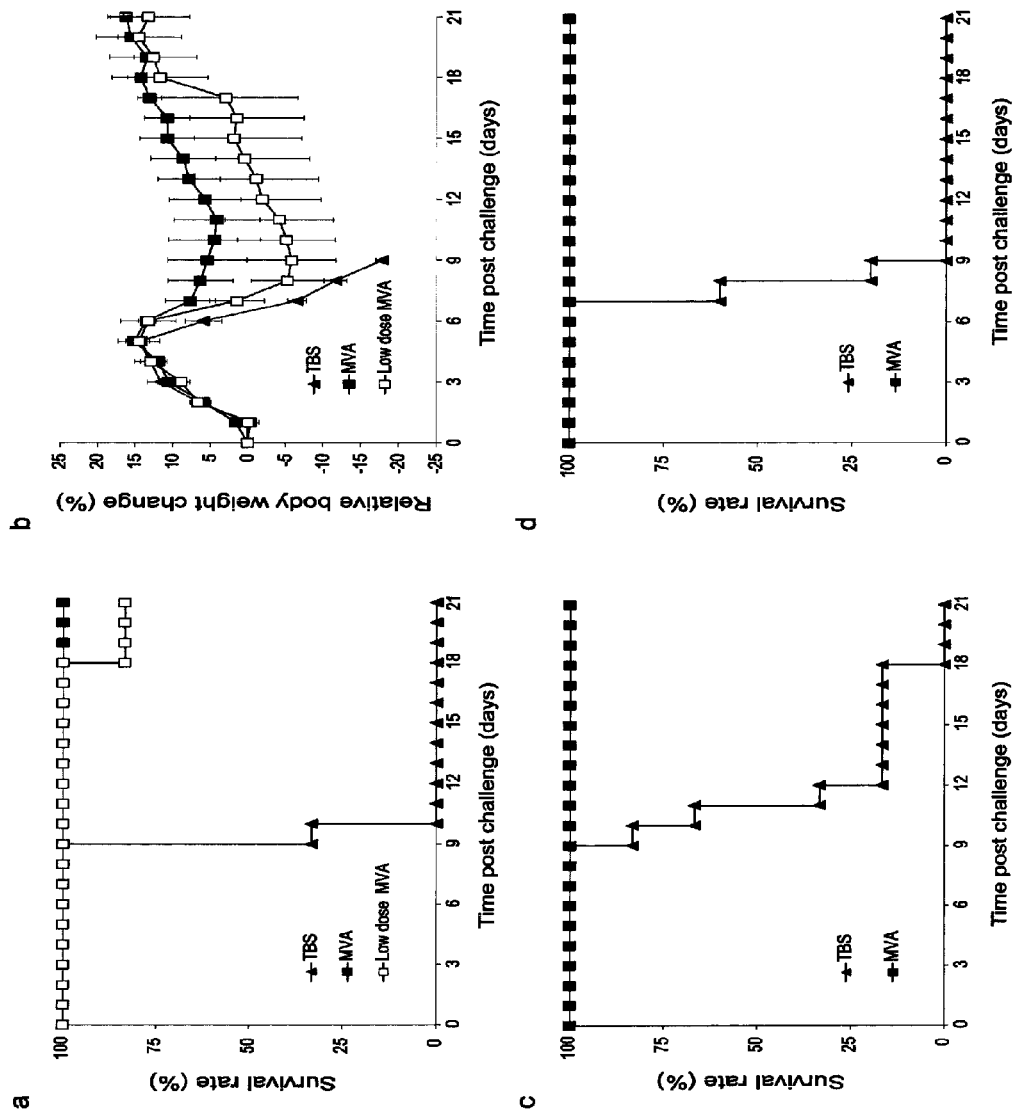
FIGS. 2*a-d* show that neonatal immunization with $10^8$ TCID$_{50}$ of an MVA induces complete protection against ECTV challenge. C57BL/6 mice were immunized with a high dose ($1 \times 10^8$ TCID$_{50}$) or low dose ($2 \times 10^6$ TCID$_{50}$) of MVA or administered TBS at birth. Four weeks after immunization, mice were challenged with $1 \times 10^4$ TCID$_{50}$ ECTV. (a) Survival and (b) relative body weight change in % (mean+/−SEM) were monitored for 21 days. Similarly, mice immunized at birth with $1 \times 10^8$ TCID$_{50}$ of MVA were challenged with (c) $3 \times 10^4$ TCID$_{50}$ ECTV 7 weeks post-immunization or (d) $1 \times 10^2$ TCID$_{50}$ ECTV 2 weeks post-immunization.

Example 9: MVA Induces Protection Against a Lethal ECTV Challenge in Two Week Old Mice In order to investigate the functionality of the T- and B-cell responses induced by MVA immunization at birth even further, the intranasal ECTV challenge model was adapted to young mice. Four weeks post-neonatal immunizations with a low or high dose of MVA, animals were challenged via the intranasal route with $1 \times 10^4$ $TCID_{50}$ ECTV. All control mice treated with placebo (Tris-buffered saline, TBS pH 7.7; 1.21 mg/ml TRIS-(hydroxymethyl)-amino-methane, 8.18 mg/ml sodium chloride) died 9 to 12 days post-challenge (FIG. 2a) with approximately 8 $Log_{10}$ ECTV plaque forming units (pfu) in their lungs, whereas all mice treated with a dose of $10^8$ $TCID_{50}$ MVA survived this otherwise lethal challenge and completely recovered after a minor transient weight loss (FIGS. 2a and 2b). All vaccinated mice had cleared ECTV from their lungs confirming complete protection. Immunization with the low dose of MVA afforded protection in 80% of the mice, despite the fact that only T-cell responses but no antibodies could be detected prior to challenge in this group (FIG. 2a). In addition to the reduced survival rate, mice immunized with the low dose showed increased disease symptoms and body weight loss (FIG. 2b) compared to those vaccinated with a dose of $1 \times 10^8$ $TCID_{50}$ of MVA. The longevity observed for B- and T-cell responses after neonatal immunization with MVA-BN (FIGS. 6 and 7) translated into long-term protection in adulthood: mice were fully protected from challenge with the lethal dose of $3 \times 10^4$ $TCID_{50}$ ECTV at the latest time point tested, i.e., 7 weeks after neonatal immunization (FIG. 2c). On the other hand, protection could already be demonstrated as early as 2 weeks after neonatal immunization, the earliest time point when ECTV challenge was technically feasible due to animal size. At this age, $10^2$ $TCID_{50}$ of ECTV killed naïve mice within 6 to 8 days, while MVA immunization at birth conferred 100% protection (FIG. 2d).

Figure 3:
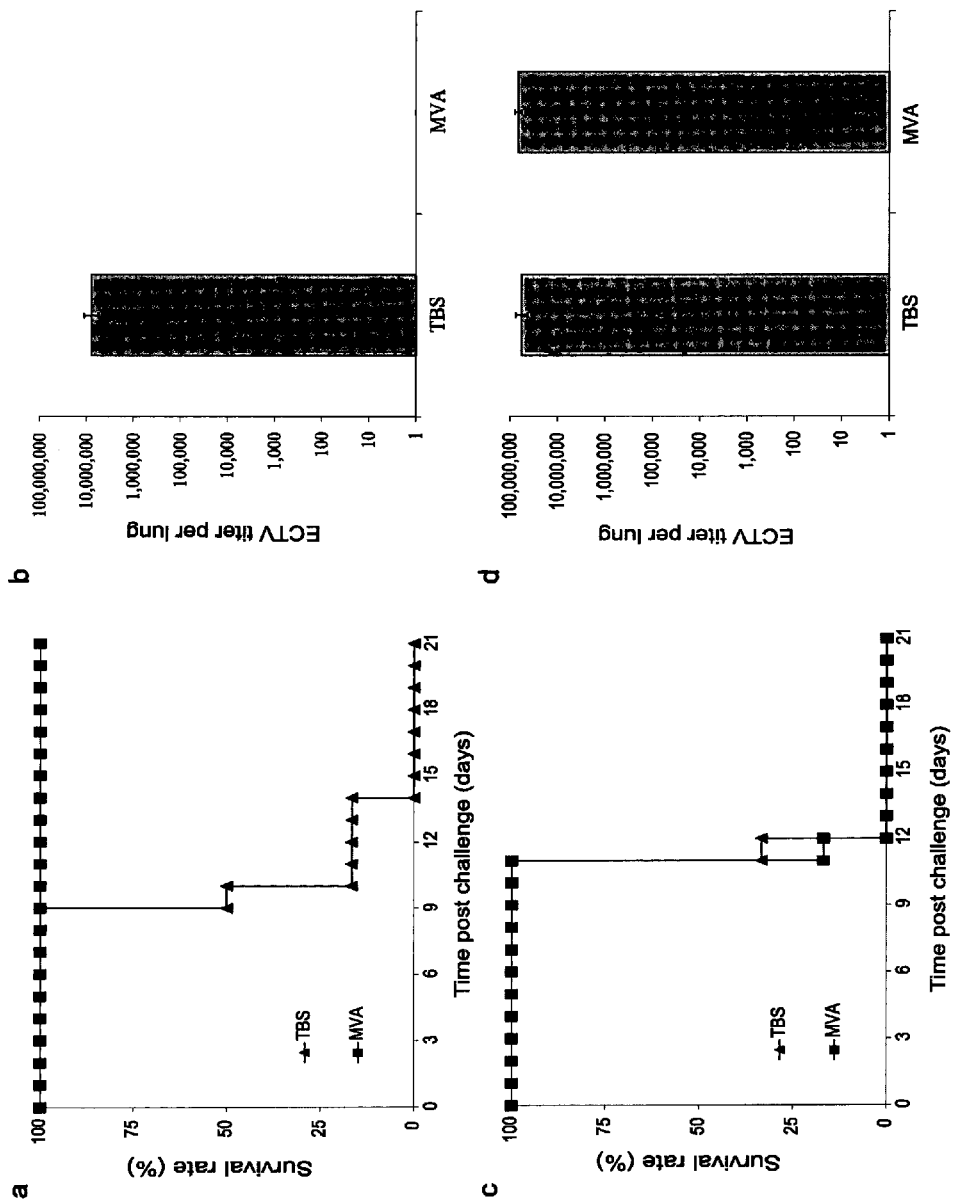
FIGS. 3*a-d* show that protection depends on the T- and B-cell immune responses. (a, b) FLT3 or (c, d) TCRβδ knockout mice were immunized at birth with $1 \times 10^8$ TCID$_{50}$ of MVA and challenged with $1 \times 10^3$ TCID$_{50}$ of ECTV 4 weeks later. (a, c) Survival was monitored for 21 days. (b, d) At the time of death or at the end of the observation period, lungs were necropsied, homogenized and the ECTV titer per lung was determined by plaque assay (GMT+/−SEM).

Example 10: Protection Against Lethal ECTV Challenge Depends on the Adaptive Immune Response It has previously been shown that injection of MVA at birth boosts early development of pDC and leukocyte precursors via an increase of FLT3 ligand (FLT3-L), which led to an increased resistance to viral infections in the first week of life. Franchini et al., J. Immunol. 172, 6304-6312 (2004); Vollstedt et al., Eur. J. Immunol. 36, 1231-1240 (2006). Therefore, the role of FLT3-L in the protection against lethal ECTV challenge was investigated using FLT3-L knockout mice. These mice have about tenfold less pDC than C57BL/6 wild type mice and are unable to up-regulate pDC. In addition, these mice lack other cell types of the innate immune system. Vollstedt et al., Eur. J. Immunol. 36, 1231-1240 (2006). FLT3-L knockout mice were immunized with MVA at birth and challenged 4 weeks later with $1 \times 10^3$ $TCID_{50}$ ECTV. All vaccinated mice survived the infection (FIG. 3a) and completely cleared ECTV from their lungs (FIG. 3b), while all non-vaccinated mice succumbed to infection. Since FLT3-L knockout mice are more sensitive to viral infection, this lower dose of $1 \times 10^3$ $TCID_{50}$ ECTV was chosen (FIG. 3a). Similar results were obtained in 2-week-old FLT3-L knockout mice. As both B- and T-cell immune responses were not affected by the reduced level of pDC and the lack of other innate cells, it clearly indicates that the innate immune system is not the sole mechanism of protection induced by MVA.

The role of the adaptive immune response in the protection afforded by neonatal immunization was investigated. T-cell receptor βδ (TCRβδ) knockout mice are devoid of T-cells and are also unable to mount a vaccinia-specific B-cell response due to the absence of T-helper cells. TCRβδ knockout mice vaccinated with MVA at birth succumbed 11 to 12 days after an intranasal challenge with $1 \times 10^3$ $TCID_{50}$ ECTV, arguing for the requirement of an adaptive immune response for protection (FIG. 3c). Similar to the FLT3-L knockout mice, this lower challenge dose was chosen based on the acute sensibility of TCRβδ knockout mice to viral infection. At death, both untreated and MVA immunized mice had a viral load in their lungs comparable to naïve wild type mice challenged with $1 \times 10^4$ $TCID_{50}$ ECTV (FIG. 3d). Using these two knockout mouse models, it was shown that the protection afforded by neonatal immunization was not due to an unspecific resistance offered by a boosted innate immunity but that it was afforded by vaccinia-specific adaptive immune responses mounted by a relatively undeveloped immune system.

Example 11: Both T- and B-Cell Responses are Required for Complete Protection

Figure 4:
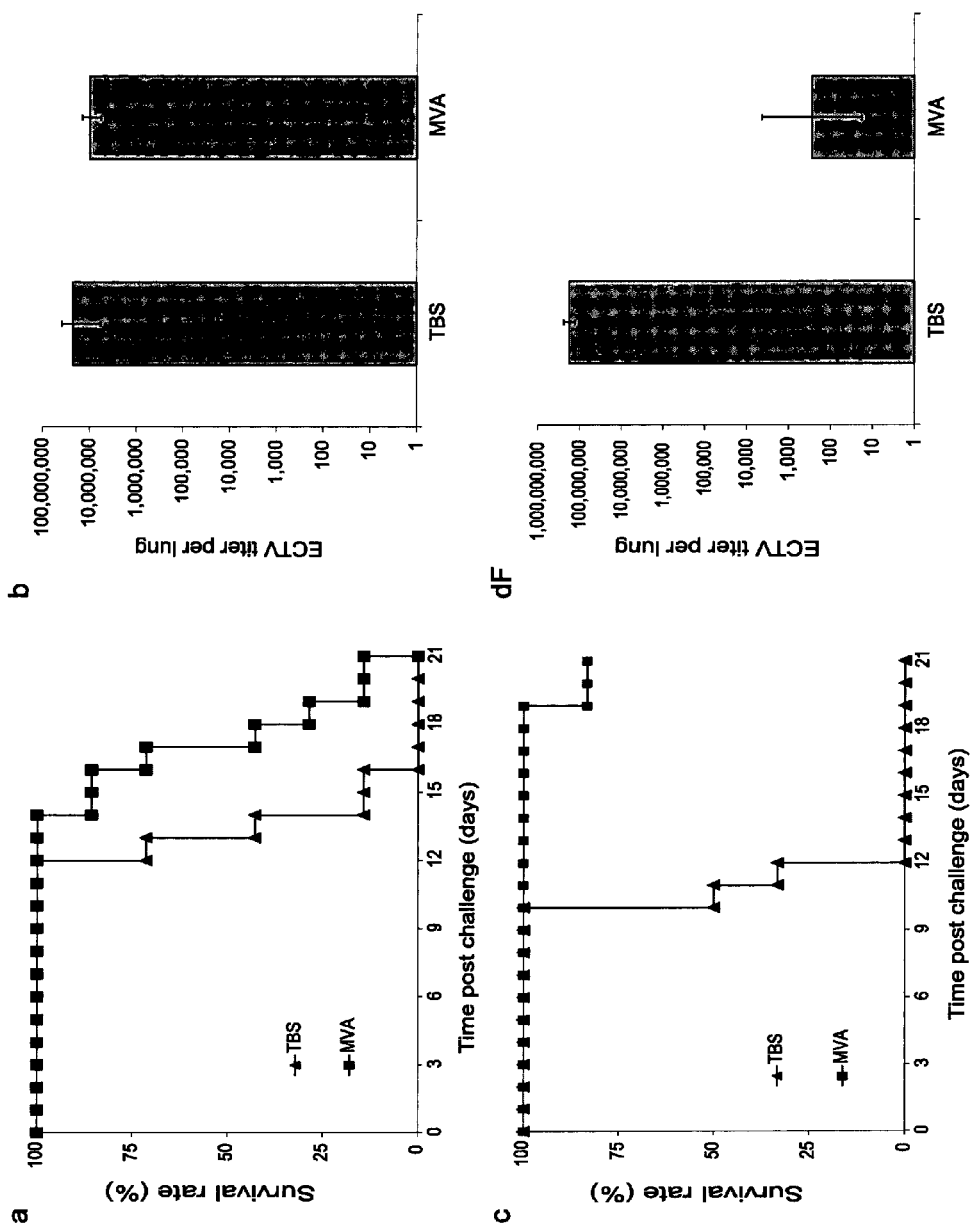
FIGS. 4*a-d* show that both T- and B-cell responses are required for complete protection (a, b) β2m knockout or (c, d) T11μMT transgenic mice were immunized at birth with $1 \times 10^8$ TCID$_{50}$ of MVA and challenged with $1 \times 10^4$ TCID$_{50}$ of ECTV 4 weeks later. (a, c) Survival was monitored for 21 days. (b, d) At the time of death or at the end of the observation period, lungs were necropsied, homogenized and the ECTV titer per lung was determined by plaque assay (GMT+/−SEM).
Figure 9:
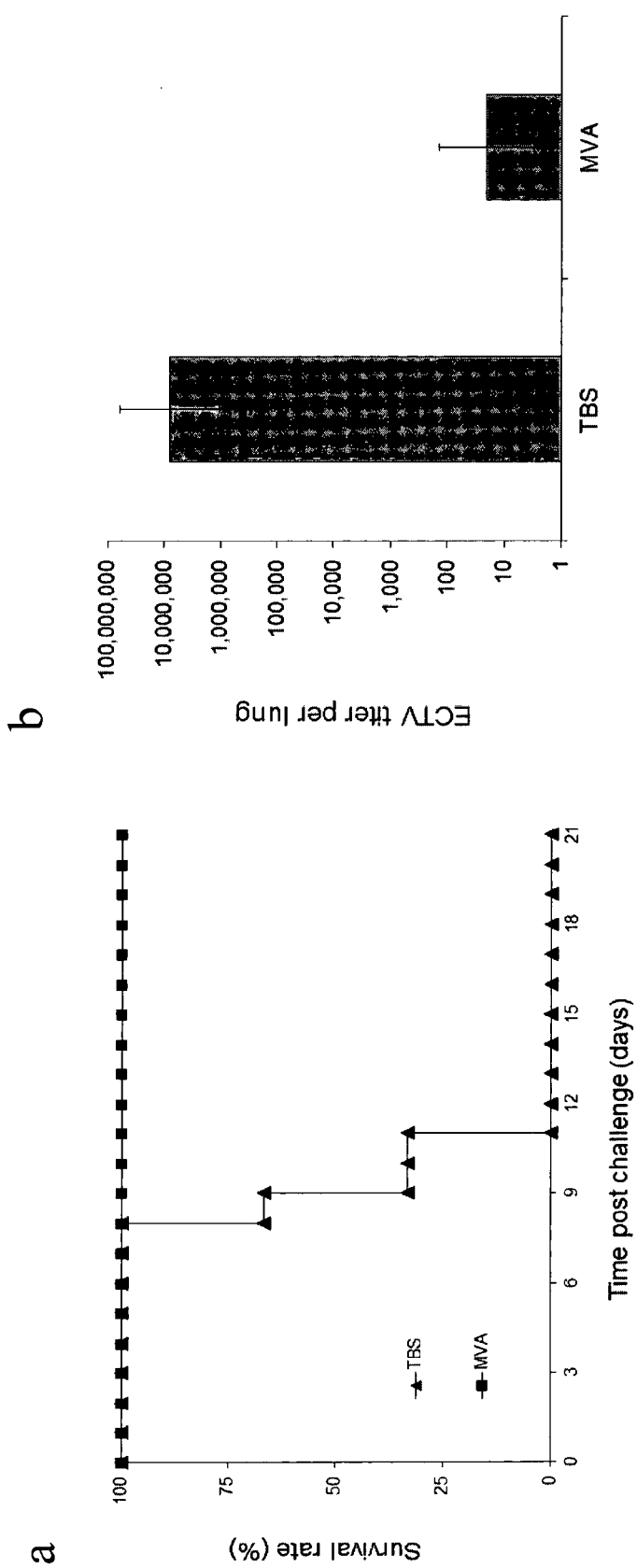
FIGS. 9a-b show that an immunoglobulin class switch is required for viral clearance. Activation-induced cytidine deaminase (AID) knockout mice were immunized at birth with $1\times10^8$ $TCID_{50}$ of MVA and challenged with $1\times10^4$ $TCID_{50}$ of ECTV 4 weeks later. (a) Survival was monitored for 21 days. (b) At time of death or at the end of the observation period, lungs were necropsied, homogenized and the ECTV titer per lung was determined by plaque assay (GMT+/−SEM).

The role of cellular versus humoral immune responses in protection was examined. The fact that 2-week-old mice were protected at a time when T-cell responses but hardly any antibodies could be detected led to the notion of a dominant role for T-cells in protection of newborn mice. Indeed, in the absence of CD8+ T-cells in β2m knockout mice, immunization with MVA did not induce protection, (FIGS. 4a and b), although antibody responses were not affected. To evaluate the need for vaccinia-specific B-cells, T11µMT genetically modified mice were utilized. These mice have a rearranged heavy chain gene specific for a VSV virus and are thus are unable to generate specific antibodies upon vaccination with MVA. In the absence of vaccinia-specific B-cell responses, one T11µMT mouse immunized with MVA died of ECTV infection two days before the end of the observation period (FIG. 4c) and only two-thirds of the mice had cleared ECTV from their lungs at the end of the 21-day observation period (FIG. 4d). Similar observations were made in AID knockout mice able to mount only IgM responses (FIG. 9). Taken together, these results reveal a primary role for cytotoxic T-cells, which requires support by antibodies to afford complete protection induced by MVA vaccination at birth.

Figure 5:
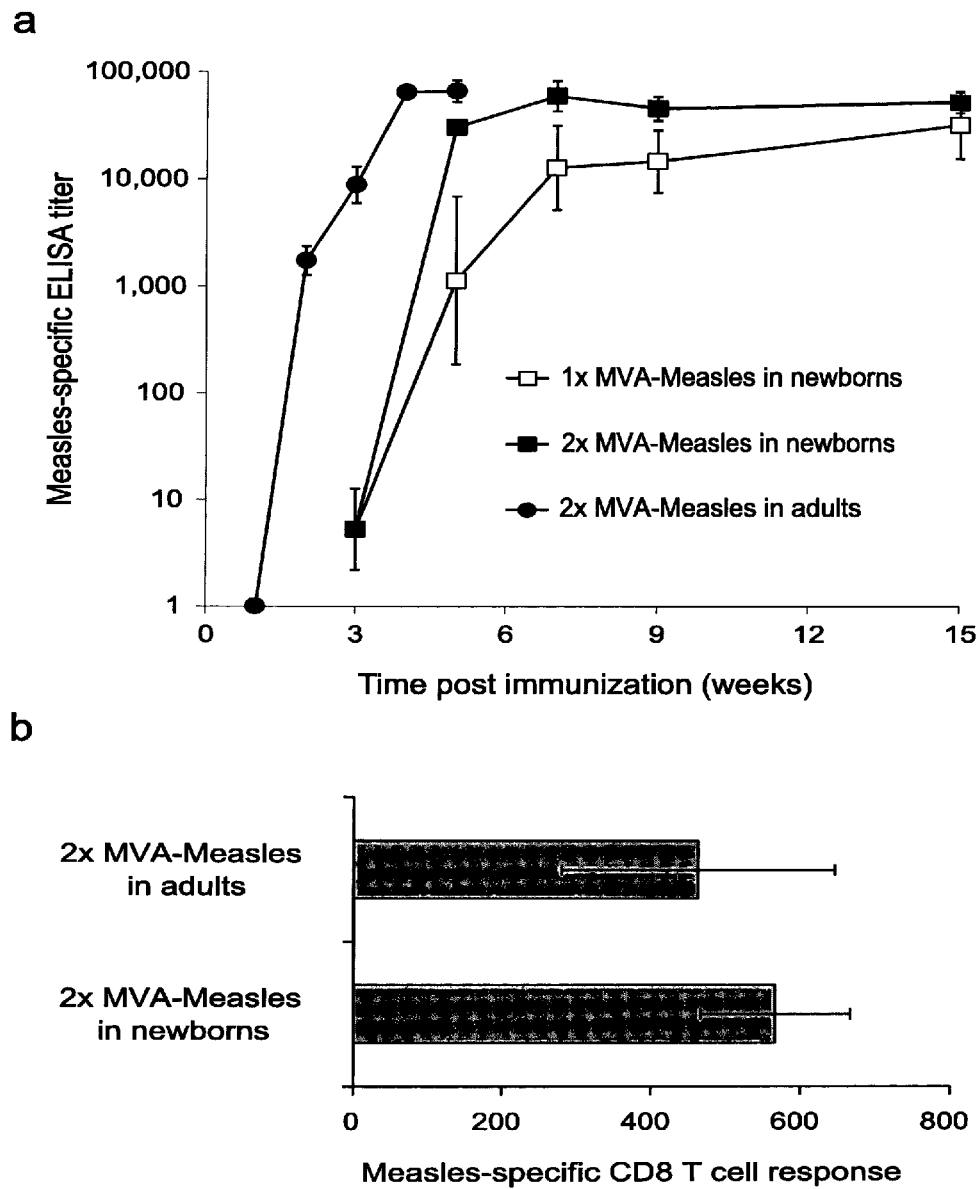
FIGS. 5*a-b* show the immunogenicity of a recombinant MVA-Measles vaccine in newborn and adult mice. (a, b) Newborn or adult BALB/c mice were immunized twice with $1 \times 10^8$ TCID$_{50}$ of MVA-Measles three weeks apart. (a) In addition, some neonates were immunized only at birth. Adult mice were bled 2, 3, 4 and 5 weeks after the first immunization, whereas newborns could be bled only 3 weeks after birth. Blood was then drawn every two weeks (four times) and again when mice were sacrificed (15 weeks after neonatal immunization). Measles-specific IgG was measured by ELISA (GMT+/−SEM). (b) Two weeks after the second immunization, measles-specific T-cells were measured after in vitro stimulation of splenocytes with a nucleocapsid-specific peptide and IFNγ-secreting cells were detected by ELISpot. (Mean of stimulation indexes+/−SEM).

Example 12: Recombinant MVA as Vector for Vaccines Against Childhood Diseases The fact that a single immunization with MVA at birth induced short and long term protective immunity suggests an opportunity for its use as viral vector to develop childhood vaccines. Therefore the potential of recombinant MVA as vaccine against childhood disease was analyzed using MVA-Measles in the neonate mouse model. MVA-Measles encodes three different measles virus proteins within the MVA backbone: the hemagglutinin- and fusion-proteins involved in binding and fusion with the host cell, as well as the nucleocapsid-protein associated with the viral single strand RNA. As seen for neonatal vaccination with MVA, recombinant MVA-Measles also elicited strong vaccinia-specific B- and T-cell responses after immunization at birth and boost 3 weeks later. More importantly, also Measles-specific B- and T-cell responses were readily detectable (FIGS. 5a and 5b). The magnitude of the response was comparable to that seen in adult mice vaccinated with MVA-Measles using the same schedule, albeit with the same 1-2 week delay in antibody responses as seen for MVA-induced vaccinia responses. Again, a single vaccination with MVA-Measles at birth led to a strong and sustained measles-specific antibody response with levels only slightly lower compared to those observed in mice receiving a booster vaccination (FIG. 5a).

The invention claimed is:

1. A method for inducing a protective immune response against a poxvirus in a human neonate or infant of less than 6 months of age comprising administering a dose of at least $10^8$ 50% tissue culture infectious dose (TCID$_{50}$) of a modified vaccinia virus Ankara (MVA) to a human neonate, wherein the administration induces protective T- and B-cell responses against a poxvirus in the human neonate prior to 6 months of age in the absence of a second administration of the MVA.

2. The method of claim 1, wherein the administration is administered to a human infant of less than 2 months of age.

3. The method of claim 1, wherein the administration is administered to a human neonate.

4. The method of claim 1, wherein the administration is administered to a human neonate within 72 hours after birth.

5. The method of claim 1, wherein the administration induces protective T- and B-cell responses against an orthopoxvirus.

6. The method of claim 1, wherein the administration induces protective T- and B-cell responses against a Vaccinia virus.

7. The method of claim 1, wherein the administration induces protective T- and B-cell responses against smallpox.

8. The method of claim 1, further comprising administering one or more boosting administrations of the MVA.

9. The method of claim 1, wherein the MVA is a recombinant MVA.

10. The method of claim 9, wherein the administration induces T- and B-cell responses against a heterologous antigen encoded by the recombinant MVA.

11. A method for inducing a protective immune response against a poxvirus in a human neonate or infant comprising administering a dose of at least $10^8$ 50% tissue culture infectious dose (TCID$_{50}$) of a modified vaccinia virus Ankara (MVA) to a human neonate or infant of less than 6 months of age, wherein the administration induces protective T- and B-cell responses against a poxvirus in the human neonate or infant within 2 weeks of the administration.

12. The method of claim 11, wherein the administration is administered to a human infant of less than 2 months of age.

13. The method of claim 11, wherein the administration is administered to a human neonate.

14. The method of claim 11, wherein the administration is administered to a human neonate within 72 hours after birth.

15. The method of claim 11, wherein the administration induces protective T- and B-cell responses against an orthopoxvirus.

16. The method of claim 11, wherein the administration induces protective T- and B-cell responses against a Vaccinia virus.

17. The method of claim 11, wherein the administration induces protective T- and B-cell responses against smallpox.

18. The method of claim 11, further comprising administering one or more boosting administrations of the MVA.

19. The method of claim 11, wherein the MVA is a recombinant MVA.

20. The method of claim 19, wherein the administration induces T- and B-cell responses against a heterologous antigen encoded by the recombinant MVA.

21. The method of claim 1, wherein MVA is MVA-BN.

22. The method of claim 11, wherein MVA is MVA-BN.

* * * * *